United States Patent [19]

Bresson-Rival et al.

[11] Patent Number: 5,989,596

[45] Date of Patent: *Nov. 23, 1999

[54] COMPOSITIONS COMPRISING A DEPIGMENTING AGENT CONSISTING OF SULFITES AND METABISULFITES AND PLANT EXTRACTS FOR USE IN INHIBITING MELANOGENESIS OR FOR DEPIGMENTING

[75] Inventors: Delphine Bresson-Rival, Lyons; Eric Perrier, Les Cotes d'Arey, both of France

[73] Assignee: Coletica, Lyons, France

[ * ] Notice: This patent is subject to a terminal disclaimer.

[21] Appl. No.: 08/906,471

[22] Filed: Aug. 5, 1997

[30] Foreign Application Priority Data

Jun. 9, 1997 [FR] France .................................. 97 07103

[51] Int. Cl.$^6$ .......................... A61K 33/04; A61K 35/78
[52] U.S. Cl. ....................... 424/711; 424/195.1; 514/783
[58] Field of Search ............................... 424/195.1, 706, 424/707, 711; 514/783

[56] References Cited

U.S. PATENT DOCUMENTS 4,847,075  7/1989  Takahashi .................................. 424/62
5,407,677  4/1995  Tominaga et al. ...................... 424/401

FOREIGN PATENT DOCUMENTS

| 296923 | 12/1988 | European Pat. Off. . | |
| 0419901 | 3/1991 | European Pat. Off. ......... | A61K 7/48 |
| 0419901 | 4/1991 | European Pat. Off. . | |
| 2088848 | 1/1972 | France . | |
| 2736263 | 1/1997 | France . | |
| 3-279313 | 12/1991 | Japan . | |
| 06263624 | 9/1994 | Japan ............... | A61K 7/48 |
| 08012565 | 1/1996 | Japan ............... | A61K 7/48 |
| WO 97/02807 | 1/1997 | Japan ............... | A61K 7/48 |

*Primary Examiner*—Kathleen K. Fonda
*Assistant Examiner*—Marjorie A. Moran
*Attorney, Agent, or Firm*—Dennison, Meserole, Scheiner & Schultz

[57] ABSTRACT

The invention relates to the use of sulfite, including metabisulfite, as melanogenesis-inhibiting or depigmenting agent. The invention enables preparing melanogenesis-inhibiting or depigmenting cosmetic compositions and optionally advantageously pharmaceutical compositions for treating pathologies.

46 Claims, No Drawings ns and metabisulfites and plant extracts for use in inhibiting melanogenesis or for depigmenting

BACKGROUND OF THE INVENTION

The present invention relates essentially to the use of sulfites or metabisulfites in cosmetics, or for manufacturing a pharmaceutical composition, notably a dermatological composition, with melanogenesis-inhibiting effect or with depigmenting activity.

The invention also covers cosmetic compositions or pharmaceutical compositions, notably dermatological compositions thus obtained, with melanogenesis-inhibiting effect or with depigmenting activity.

The invention further covers a method of cosmetic depigmenting treatment which uses sulfites or metabisulfites as actives towards depigmentation.

It is known that in order to fight against sun's rays, the skin possesses different cells which are particularly adapted to this function: melanocytes.

During a complex process, melanogenesis, these cells produce a dark pigment, melanin, the effect of which is to protect the cutaneous structures and to increase the time needed for contracting sun-burn.

However, not every one of the melanins is protective, and there exists in particular a form of melanin, called phaeomelanin, which is extremely phototoxic. Capable as every melanin is of reacting with certain forms of free radicals, phaeomelanin causes the formation of free radicals which are even more toxic, which can cause irreversible damage to the genetic material of the keratinocytes.

On the other hand, certain disorders linked to a disfunctioning of the melanization unit can cause a hyper-pigmentation which is sometimes unaesthetic.

Thus, the use of inhibitors of melanin synthesis is particularly interesting in cosmetics, not only for applications wherein a real depigmentation is sought-after, as in the case of the blanching of highly pigmented skin or the inhibition of hyper-pigmentation in certain unaesthetic aspects for example, but also for applications aiming at lightening the tint, giving brightness to the skin, and a sparkle to the surface tissues.

This inhibition of the melanin synthesis may also be particularly interesting within the context of therapeutic treatment for treating a real pathology.

The invention does however aim at a simple cosmetic use although a pharmaceutical use within the context of pathology treatment is also envisaged and is also part of the invention.

DESCRIPTION OF THE PRIOR ART

Various cosmetic or optionally pharmaceutical compositions have already been proposed.

The GB-A-1 349 955 document from 1974 may be cited as an example of prior art, which describes a skin paling composition with synergetic action which contains hydroquinone, an exfoliating-irritant agent which is particularly a long-chain fatty acid ester of an unsaturated fatty acid, alkylamines, and an anti-inflammatory corticosteroid such as fluorometholone, deamethasone or hydrocortisone.

On the other hand, the Romanian document RO-81370, WPIL abstract AN-83-762909 relates to an emollient cream for removing colored marks from the skin which is based on cetazole, Vaseline, lanolin, an excipient comprising anti-oxidant stabilizers such as metabisulfite ($Na_2S_2O_5$).

The JP-A-58198421 document, WPIL abstract AN-84-002869, also describes a skin paling composition for treating skin diseases, which contains liver oil, a composition containing basic sulfur compounds, a composition comprising hydrogen peroxide, salicylic acid and an acidic composition containing a bromate. The liver oil can be obtained from fish liver oil, examples of sulfur-containing compounds are thioglycolic acid, thiolactic acid, thiopropionic acid, thiosalicylic acid and thiobutyric acid, preferably in the form of a salt with various amines, or sodium bisulfite, and cysteine. Ammonium thioglycolate is especially preferred.

Furthermore, it is even known from the US-A-692,261 document of a dermal preparation for external application having a melanogenesis-inhibiting activity which comprises kojic acid or a kojic acid derivative as well as sodium metabisulfite or sodium hydrogen sulfite and/or hydrogen peroxide.

It is specified that the discolouration of the preparation is prevented during or after storage for a long period of time by the incorporation of sodium hydrogen sulfite and/or hydrogen peroxide so as to maintain the commercial value of the preparation.

From this, the use of sodium hydrogen sulfite or sodium metabisulfite is only envisaged as a stabilizer of the coloration of the preparation and not as an active agent for inhibiting the activity of tyrosinase, a fundamental enzyme in melanogenesis.

Further, the JP-A-04/082834 document from 1992, WPIL abstract AN-92-138630, describes a medicament which contains galactosamine or a salt and/or mannosamine or a salt with various excipients containing stabilizers of which are sodium hydrogen sulfite or sodium metabisulfite at a proportion of 0.05%.

Further, the JP-A-07/025742 document from 1995 relates to a skin paling cosmetic composition which contains ascorbic acid derivatives, hydroquinone derivatives and/or plant extracts and/or placenta extracts as active principle as well as sulfur-containing stabilizers, notably a hydrogen sulfite salt, in order to prevent the coloration of the preparation.

In summary, the prior art has used metabisulfite or hydrogen sulfite only as an anti-discoloration agent or stabilizer, but in no case as melanogenesis-inhibiting active principle.

SUMMARY OF THE INVENTION

The principal aim of the invention is to solve the problem consisting of providing a cosmetic composition or advantageously also a pharmaceutical composition, notably a dermatological composition, with melanogenesis-inhibiting effect, which enables obtaining a depigmenting activity for a cosmetic use and advantageously independently for a pharmaceutical and/or dermatological use within the context of pigmentation pathology.

A further aim of the present invention is to solve the novel technical problem which consists of providing a cosmetic composition and advantageously a pharmaceutical composition, notably a dermatological composition, with an inhibiting effect on tyrosinase, a fundamental enzyme in melanogenesis which should be particularly stable, notably in the pH ranges preferred by the person skilled in the art working in the cosmetic field, i. e. pHs between about 5 and about 8.

A further aim of the invention is to solve the novel technical problems stated above with the aid of a solution which enables obtaining cosmetic and advantageously pharmaceutical compositions, notably dermatological compositions, of very high stability, and without emitting smell.

A further aim of the invention is to solve the numerous technical problems stated above, according to a particularly simple solution which necessitates a small number of melanogenesis-inhibiting active principles, in a limited amount, which is particularly easy to carry out and which can be manufactured on an industrial and cosmetic or advantageously also pharmaceutical, notably dermatological scale.

The whole of these technical problems is solved for the first time in a simultaneous manner by the present invention.

Thus, within the context of the present invention, it has been discovered in a particularly unexpected manner that sulfites, including metabisulfites, possess an inhibiting activity of tyrosinase, a fundamental enzyme in melanogenesis, in procuring to the formulations containing them a particularly interesting depigmenting activity, principally for a cosmetic use but also advantageously enabling pharmaceutical and notably dermatological use within the context of the treatment of skin pathology.

Within the context of the present invention, it has been possible to demonstrate in an unexpected manner that sulfites, including metabisulfites, enable preventing an excessive pigmentation by intervening in a reduction of the activity of tyrosinase.

Thus, according to a first aspect, the present invention relates to the use of sulfites, including metabisulfites, as cosmetic agent with inhibiting activity of tyrosinase, a fundamental enzyme in melanogenesis, or with depigmenting activity.

According to a second aspect, the present invention also covers the use of sulfites, including metabisulfites, for manufacturing pharmaceutical compositions and notably dermatological compositions with melanogenesis-inhibiting activity or depigmenting activity.

According to a third aspect, the present invention also covers a cosmetic composition or a pharmaceutical composition, notably a dermatological composition, which comprises as melanogenesis-inhibiting active agent or depigmenting active agent an effective amount with this aim in view of at least one sulfite, including a metabisulfite.

According to a fourth aspect, the present invention also covers a melanogenesis-inhibiting or depigmenting cosmetic treatment method, wherein it comprises the topical application, of a composition containing an effective amount with this aim in view of at least one sulfite, including a metabisulfite, as melanogenesis-inhibiting or depigmenting active principle, onto the areas concerned of an animal, advantageously a human being.

The invention, according to a fifth aspect, also covers a method of therapeutic treatment, notably dermatological treatment, of an animal, advantageously a human being, wherein it comprises the application of an effective amount with this aim in view of at least one sulfite, including a metabisulfite, as melanogenesis-inhibiting or depigmenting active principle, onto the areas concerned of the skin.

Within the context of the present invention, whether it be in the description or the claims, the expression "sulfite" includes any sulfite or sulfite derivative, and particularly sulfite salts, particularly with alkali or alkaline earth metals, preferably with alkali metals such as sodium or potassium. Sodium is currently of preferred advantage.

On the other hand, the expression also includes sulfite partial salts such as metabisulfites or hydrogen sulfites, in particular with alkali or alkaline earth metals, preferably with alkali metals and particularly sodium or potassium, preferably sodium.

Within the context of any one of the aspects of the invention, the proportion of sulfite incorporation is between 0.001% and 20%, advantageously between 0.01% and 10% by weight.

Furthermore, according to a particularly advantageous embodiment of the invention, the sulfites, including the metabisulfites, of the present invention, are used in combination with at least one plant extract.

Within the context of the invention, any plant extract can be used.

However, it is preferred to use a plant extract selected from the group consisting of a mulberry extract, a lemon extract, a saxifrage extract, a grapefruit extract, a grape extract, and an oughon extract.

The proportions of incorporation of such extracts ranges within large limits. The total proportion of extract can constitute the principal part of the composition.

Generally, the proportion of extract shall be between 0.01% and 90%, better between about 5% and 70% of the total weight of the composition. It is preferred to use combinations of extract. Each extract being present in proportions of at least about 5% and not more than about 30% in order to use at best the advantages procured by each extract, these advantages being well apparent to the person skilled in the art.

It has been possible to demonstrate in a particularly unexpected manner that the presence of plant extracts results in an efficient stabilization of the sulfites, including metabisulfites.

It has indeed been observed that the sulfites, including the metabisulfites, used as such in a cosmetic solution induce the appearance of smells unacceptable from a cosmetic point of view, smells which are particularly sensitive to pHs between 5 and 7 or even to more acidic pHs.

Now, when these sulfites are combined with plant extracts, these plant extracts mask the smell given off by the sulfites, including when these are placed at conventional pHs of the cosmetic or pharmaceutical, notably dermatological composition.

Furthermore, it has also been possible to observe that the active principles thus prepared are perfectly well tolerated in the cosmetic and even advantageously pharmaceutical, notably dermatological compositions, and possess an extremely low cytotoxicity, more than 200 times lower than that of the depigmenting actives usually used and such as exemplified by the prior art stated above, notably that used in cosmetics such as hydroquinone or kojic acid.

It is to be noted that the prior art molecules have their activity which lies on the observation of a very rapid paling of the skin based on the degradation of the organized structures of the melanin.

Most of these products have revealed to be corrosive, cytotoxic, even sensitizing, this strongly limiting their use in cosmetics now.

Furthermore, if kojic acid, ascorbic acid and their derivatives are extremely effective in the selective blockage of the activity of tyrosine, these molecules are very unstable in complex media, that cosmetic formulations are, and oxidize rapidly to colored decomposition products which are little compatible with the organoleptic characters usually sought after for cosmetic formulations.

Furthermore, although without any common measure with that observed for hydroquinone and linoleic acid, a certain toxicity is obtained with products of the kojic acid or ascorbic acid type.

It has been discovered by the inventors in a particularly unexpected manner that sulfites, including metabisulfites, are not only very effective in inhibiting tyrosinase, and therefore melanogenesis, and thus possess a very significant depigmenting activity, but also have an absence of cytotoxicity which constitutes a determining technical advantage.

On the other hand, the sulfites, including the metabisulfites, possess an excellent stability as a function of pH and temperature, and enable satisfying the organoleptic criteria usually sought after mainly in cosmetics and also advantageously in pharmacy and notably in dermatology, when they are combined with at least one plant extract.

Naturally, the invention can be combined with various other active principles having melanogenesis-inhibiting activity or not, as well as with various cosmetically or pharmaceutically, notably dermatologically acceptable carriers so as to obtain cream or lotion formulations capable of lightening the skin without any danger to the user.

Thus, the cosmetic or pharmaceutical, notably dermatological compositions can be prepared to have a pH between about 5 and about 8.

As has been indicated above, such compositions are perfectly stable and do not develop a smell even after several months of storage.

Other aims, characteristics and advantages of the invention appear clearly with the aid of the explanatory description which makes reference to various examples of effectiveness and/or formulation tests, given only as illustration and in no way therefore limit the scope of the invention.

The Examples make up an integral part of the present invention and any characteristic which appears novel compared to any state of the prior art from the description taken as a whole, including the Examples, make up an integral part of the invention in its function and in its generality.

Thus, every Example is of general scope.

On the other hand, in the Examples, all the percentages are given by weight, unless otherwise indicated, ambient temperature is expressed in degrees Celsius unless otherwise indicated, and the pressure is atmospheric pressure, unless otherwise indicated.

EXAMPLE 1 OF THE INVENTION

In Vitro Test of the Inhibition of Isolated Tyrosinase by Sodium Sulfite

It is known that tyrosinase is capable of catalyzing the formation of L-Dopaquinone and then dopachrome from L-Dopa. Now, dopachrome is a colored compound whose appearance is possible to follow by UV visible spectrophotometry at 475 nm. The use of an active capable of modifying the enzymatic activity manifests itself by a variation of the rate of appearance of this colored molecule.

The ratio of the rates of formation of dopachrome enable precisely determining the activations or the inhibitions obtained with the different molecules tested.

Within the context of the present in vitro test, sodium sulfite was used in this test at the concentrations of 0.01%, 0.1%, 1% and 10% respectively, and the results obtained on the inhibition of tyrosinase are given in Table I below:

TABLE I

| Concentration level | 0.01% | 0.1% | 1% | 10% |
|---|---|---|---|---|
| Results (inhibition) | 93.7% | 100% | 100% | 100% |

Organoleptic tests have even been carried out on 5% sodium sulfite solutions or with 10% of a mulberry extract or 10 or with 20% with a lemon extract. These tests were led over 4 weeks at 45° C. at pH 5.5 and 6.5. The results are given in Table II below:

TABLE II

| | 4 weeks at 45° C. | | |
|---|---|---|---|
| | Na sulfite (5%) | Na sulfite (5%) + mulberry extract (10%) | Na sulfite (5%) + lemon extract (20%) |
| pH 5.5 | extremely strong smell | absence of smell | absence of smell |
| pH 6.5 | very strong smell | total absence of smell | total absence of smell |

It is clearly seen from Table I that sodium sulfite inhibits almost all the tyrosinase even at a proportion as weak as 0.01%, while in Table II the presence of smell is prevented by adding a plant extract, e. g. a mulberry extract or a lemon extract, each one of these activities being particularly unexpected for a person skilled in the art.

EXAMPLE 2 OF THE INVENTION

Test of Inhibition of Isolated Tyrosinase by Sodium Metabisulfite

In this test, sodium metabisulfite was used at concentrations of 0.01%, 0.1%, 1% and 10% and the results obtained on tyrosinase inhibition are given in Table III below:

TABLE III

| Concentration level | 0.01% | 0.1% | 1% | 10% |
|---|---|---|---|---|
| Results (inhibition) | 92.8% | 100% | 100% | 100% |

It is also noted that sodium metabisulfite has an almost total effect of tyrosine inhibition even at a concentration as low as 0.01%.

Also, organoleptic tests are then carried out on 5% sodium metabisulfite solutions with or without either 20% of a saxifrage extract or 10% of a grapefruit extract. These tests were led over 4 weeks at 45° C. at pH 5.5 and 6.5. The results are given in Table IV below:

TABLE IV

| | 4 weeks at 45° C. | | |
|---|---|---|---|
| | Na metabisulfite (5%) | Na metabisulfite (5%) + saxifrage extract (20%) | Na metabisulfite (5%) + grapefruit extract (10%) |
| pH 5.5 | extremely strong smell | absence of smell | absence of smell |

TABLE IV-continued

| | 4 weeks at 45° C. | | |
|---|---|---|---|
| pH 6.5 | very strong smell | total absence of smell | total absence of smell |

As for Example 1, it is noted that the presence of a plant extract, here a saxifrage extract or a grapefruit extract enables preventing the formation of smells during prolonged storage over 4 weeks at 45° C. at a pH of 5.5 or 6.5, which is particularly unexpected for a person skilled in the art.

EXAMPLE 3 OF THE INVENTION

Inhibition of Tyrosinase by Potassium Sulfite

In this test, potassium sulfite was used at concentrations of 0.01%, 0.1%, 1% and 10% and the results obtained on tyrosinase inhibition are given in Table V below:

TABLE V

| Concentration level | 0.01% | 0.1% | 1% | 10% |
|---|---|---|---|---|
| Results (inhibition) | 82.7% | 98.10% | 92.7% | 100% |

It is noted from Table V above that potassium sulfite enables obtaining an inhibition of more than 80%, even at a proportion as low as 0.01%, an almost complete inhibition from proportions of 0.01%, which is remarkable.

Organoleptic tests were also carried out on 5% potassium sulfite solutions with or without either 20% of a grape extract, or 10% of an oughon extract. It is to be noted that oughon is also called Scutelaria. These tests were led over 4 weeks at 45° C. at pH 5.5 and 6.5. The results are given in Table VI below:

TABLE VI

| | 4 weeks at 45° C. | | |
|---|---|---|---|
| | K Sulfite (5%) | K Sulfite (5%) with grape extract (20%) | K sulfite (5%) with oughon extract (10%) |
| pH 5.5 | extremely strong smell | absence of smell | absence of smell |
| pH 6.5 | very strong smell | absence of smell | absence of smell |

Here again, it is noted that the presence of a plant extract, here a grape extract or an oughon extract, enables removing the presence of a smell during prolonged storage at a pH of 5.5 or 6.5.

EXAMPLE 4 OF THE INVENTION

Test of Inhibition of Tyrosinase by Potassium Metabisulfite

In this test, the potassium metabisulfite was used at concentrations of 0.01%, 0.1%, 1% and 10% and the results obtained on tyrosinase inhibition are given in Table VII below:

TABLE VII

| Concentration level | 0.01% | 0.1% | 1% | 10% |
|---|---|---|---|---|
| Results (inhibition) | 91.81% | 93.63% | 100% | 100% |

It is noted from Table VII that potassium metabisulfite inhibits tyrosinase at more than 90%, i. e. almost totally, at a concentration as low as 0.01% by weight, which is still remarkable.

Organoleptic tests are then carried out on 5% potassium metabisulfite solutions with or without either 10% of a saxifrage extract, or 5% of an oughon extract +10% of a grapefruit extract. These tests were also led over 4 weeks at 45° C. at pH 5.5 and 6.5. The results are given in Table VIII below:

TABLE VIII

| | 4 weeks at 45° C. | | |
|---|---|---|---|
| | K Metabisulfite (5%) | K Metabisulfite (5%) + saxifrage extract (10%) | K Metabisulfite (5%) + oughon extract (5%) + grapefruit extract (10%) |
| pH 5.5 | extremely strong smell | absence of smell | absence of smell |
| pH 6.5 | very strong smell | total absence of smell | total absence of smell |

It clearly emerges from Table VIII that the presence of a plant extract, e. g. a saxifrage extract or an oughon extract combined with a grapefruit extract, enables preventing the presence of a smell during a long period of storage at a pH of 5.5 and 6.5 at a temperature of 45° C.

EXAMPLE 5 OF THE INVENTION

Example of Formulation of a Composition Usable Principally as a Cosmetic Composition but also being able to be used as a Pharmaceutical or Dermatological Composition The following composition is prepared in a conventional manner from the following active ingredients:

| | |
|---|---|
| sodium sulfite | 5% |
| sodium metabisulfite | 5% |
| saxifrage extract | 25% |
| grape extract | 30% |
| mulberry extract | 5% |
| oughon extract | 5% |
| EDTA | 0.5% |
| demineralized water | QS for 100% |

The anti-tyrosinase activity was measured, for various concentrations of this composition, by simple dilution with demineralized water.

a) at a concentration of 0.015%, the composition inhibits already 21.6% of the tyrosinase activity;
b) at a concentration of 0.02%, the composition inhibits 46% of the tyrosinase activity;
c) at 0.5% the composition inhibits 93% of the tyrosinase activity.
d) at 1%, the composition inhibits 97% of the tyrosinase activity e) at a concentration equal or greater than 5%, the composition totally inhibits the tyrosinase activity.

This composition used pure has an excellent stability at ambient temperature and at 45° C. After 4 weeks of stability at 45° C., the compositions have no smell at the two pHs considered, i. e. at pH 5.5 and pH 6.5.

This composition can therefore constitute a basic or final cosmetic composition, or advantageously also a pharmaceutical and notably dermatological composition with anti-tyrosinase activity or melanogenesis-inhibiting activity or else depigmenting activity.

EXAMPLE 6 OF THE INVENTION

In Vivo Test of the Anti-Tyrosinase Activity of the Composition of the Invention of Example V An evaluation of the anti-tyrosinase activity of the composition described in Example 5 is carried out with the aid of an ex vivo tissue model on human skin explant. In this model, the evaluation of the tyrosinase activity is demonstrated by a histochemical study based on the treatment of the explant by a solution of L-Dopa, substrate of tyrosinase. The oxidation of L-Dopa by the tyrosinase produces, in the melanocytes, a black pigment precursor of melanin which is easily detectable by optical microscopy with white light. The tyrosinase activity is determined by the intensity of the calorimetric reaction obtained.

Principle of the Study

The human skin explants originate from a plastic surgery of the abdomen performed on a 27-year old woman.

The composition of Example 5 is tested at 0.1%, 1% and 10% (v/v) in ultra-pure water. A positive control and a negative control are also carried out in parallel. The positive control selected for this study is hydroquinone at 0.55% (w/v), recognized for having a very high depigmenting activity and listed amongst the active OTCs. Although not possessing any anti-tyrosinase activity, this molecule inhibits the formation of melanic pigments in the melanocytes, this enabling recommending its use in this study.

The various products in the study are incubated in the presence of L-DOPA (0.05 M) for 15 hours at 37° C.

After fixing and inclusion in paraffin, the sections are colored with hemalun/eosin/saffron and with cresyl violet, they are then observed in white light by optical microscopy.

The melanic pigments, formed via the oxidation of exogenous L-DOPA by endogenous tyrosinase, are observed. The tyrosinase activity is determined by the intensity of the calorimetric reaction obtained.

Photographic negatives, representative of the effect observed were made.

The observation of the control explant treated with L-DOPA enables demonstrating the presence of active melanocytes, i. e. possessing a tyrosinasic activity in the basal layer of the epidermis of the donor.

Used as reference product, hydroquinone at 0.55% (w/v) totally inhibits the formation of melanic pigments. This expected result validates the study carried out.

The composition of Example 5, tested at 0.1%, 1% and 10% (v/v) itself also totally inhibits the histochemical reaction.

In conclusion, under the retained experimental conditions, and at the three concentrations studied, the composition of Example 5 totally inhibits the enzymatic activity of the tyrosinase. This inhibition is exceptionally strong since the use of 0.1% of the composition of Example 5 allows a level of inhibition comparable to that obtained with 0.55% hydroquinone, a recognized but extremely cytotoxic depigmenting active compound.

This result of the invention is particularly surprising.

The cytotoxicity of the composition of the invention is the subject of the test of Example 7 below.

EXAMPLE 7 OF THE INVENTION

Test of Cytotoxicity of the Composition of Example 5 Towards Melanocytes

The preparation prepared in Example 5 is tested for its toxicity towards melanocytes.

The melanocytes of the G361 line (human melanoma) were cultivated in MacCOY medium, from GIBCO®, completed with 10% (v/v) of fetal calf serum, 50 IU/ml penicillin, 50 µg/ml streptomycin and 2 mM glutamine.

The cells were sown in 24-well culture plates at the rate of $3 \cdot 10^5$ cells per well. The product of Example 5 at various concentrations is added directly to the culture medium. After 72 hours of incubation in the presence of the product of Example 5, the cytotoxicity is evaluated by determination of the total intracellular proteins.

The results show, in every case, a relationship between the concentrations used during these tests and cytotoxicity. They also show that the cytotoxicity of the product of Example 5 towards melanocytes is between 1 and 10 mg/ml.

These values are to be compared to those described in the literature by MAEDA & FUKUDA in "In vitro effectiveness of several whitening cosmetic components in human melanocytes", published in J. Soc. Cosmeti. Chem. 42, pages 361–368 (1991) wherein the calculation of the inhibiting concentration for which half of the cells placed in culture are no longer living ($IC_{50}$) shows the very high cytotoxicity towards human melanocytes:

hydroquinone, having an $IC_{50}$ of $5.5 \ 10^{-3}$ mg/ml;

linoleic acid having an $IC_{50}$ of $2.8 \ 10^{-3}$ mg/ml, and ascorbic acid having an $IC_{50}$ of 0.88 mg/ml.

From this, the invention enables one to obtain a cytotoxicity about 1,000 times lower than that of hydroquinone or linoleic acid.

The cytotoxicity is lower than that of ascorbic acid.

EXAMPLE 8 OF THE INVENTION

Toxicological Studies

The oral toxicity test, the ocular irritation test and the skin irritation test were carried out according to the details below:

A. Oral Toxicity

This test is carried out according to the protocol established by the directives of the OECD relating to the study of the acute oral toxicity, published under the No. 401 of the Feb. 24, 1987.

Tests were carried out on the composition of Example 5 at maximal doses of 5 g per kilogram body weight, and caused no mortality.

The product of the invention such as described in Example 5 used pure and orally at doses lower than 5 g/kg do not therefore possess any abnormal oral toxicity.

B. Ocular Irritation

The ocular irritation test is carried out according to a protocol in accordance with the directives of the OECD relating to the study of the acute irritant/corrosive effect upon the eyes, such as published in No. 405 of the Feb. 24, 1987.

The product of the invention such as described in Example 5 instilled pure appear non-irritant to the eyes in the sense of the Directive 91/326 EEC.

C. Skin Irritation

This test of skin irritation was carried out according to the protocol in accordance with the directives of the OECD in relation to the study of the acute irritant/corrosive effect upon the skin, published under the number 404 of the Jul. 17, 1992.

The product of the invention such as described in Example 5, applied pure appear non-irritant to the skin in the sense of the Directive 91/326 EEC.

D. Hypoallergenicity Tests

Tests of maximization were carried out according to a protocol adapted from the method described by Magnusson & Kligman (J. Invest. Derm. 52, 268–276. 1969).

The composition of Example 5, used pure, caused no significant sensitization reaction. This composition is thus considered to be hypoallergenic, Class I.

EXAMPLE 9 OF THE INVENTION

Use of Products of the Invention in Water-in-Oil Emulsion Cosmetic Formulations for Cosmetic or Pharmaceutical Use A water-in-oil emulsion is prepared from the four following groups of components A, B, C, D in percentages by weight:

| Group A | |
|---|---|
| Butylene glycol | 2 |
| Glycine | 3 |
| Sodium dihydroxycetylphosphate, isopropyldihydroxycetylether | 2 |
| Water | QS for 100 |
| Group B | |
| Se glycostearate | 14 |
| Triisononanoin | 5 |
| Octyl cocoate | 6 |
| Group C | |
| Butylene glycol | 2 |
| Mixture of parabenses in the form of methyl, ethyl and propyl parabens | 2 |
| pH adjusted to 5.5 with a diluted strong acid or weak acid | |
| Group D | |
| Composition of the invention of Example 5 | 0.01–10% |

Mixing of the components of group A is started by heating with stirring to a temperature of about 75° C. The elements of phase B are also separately mixed and heated at the same temperature of about 75° C. The phase B is introduced into phase A under vigorous stirring and the components of groups C and D are then added successively after having been cooled to about 30° C. For group C, the pH is adjusted to 5.5 with an acid diluted in water, such as citric acid.

This composition can be applied directly on skin marks via a brush or an applicator in order to allow them to disappear progressively, a disappearance effect which can generally be observed after about two weeks. Application can also be made more generally onto the areas of the skin on which it is desired to inhibit melanogenesis or to depigment.

EXAMPLE 10 OF THE INVENTION

Use of the Products of the Invention in Cosmetic Formulations in the Form of Oil-In-Water Emulsion for Cosmetic or Pharmaceutical Use As for the preceding Example, an emulsion of the oil-in-water type is prepared from the 5 following groups of components A, B, C, D and E:

| Group A | |
|---|---|
| PEG 36-dipolyhydroxystearate | 3 |
| Capric triglyceride | 3 |
| Cetearyl octanoate | 4 |
| Dibutyl adipate | 3 |
| Grape seed oil | 1.5 |
| Jojoba oil | 1.5 |
| Phenoxyethanol in a mixture with parabens in the form of methyl, ethyl, propyl and butyl parabens | 0.5 |
| Group B | |
| Glycerine | 3 |
| Butylene glycol | 3 |
| Magnesium sulfate | 0.5 |
| EDTA | 0.05 |
| Water | QS for 100 |
| Group C | |
| Cyclomethicone | 1 |
| Dimethicone | 1 |
| Group D | |
| Perfume | 0.3 |
| Group E | |
| Composition of the invention of Example 5 | 0.01–10% |

The components of group A are mixed together by adding them successively in the order indicated while heating them to about 75° C. Carried out separately for the components of group B in heating them also at a temperature of about 75° C. Afterwards, group B is introduced into group A under vigorous stirring and then left to cool to ambient temperature and finally, the components of groups C, D and E are added when the temperature is about 30° C.

This composition can be applied directly on the skin marks via a brush or an applicator in order to allow them to disappear progressively, a disappearance effect which can generally be observed after about two weeks. Application can also be made more generally onto the areas of the skin on which it is desired to inhibit melanogenesis or to depigment.

EXAMPLE 11 OF THE INVENTION

Cosmetic or Pharmaceutical Composition in the Form of Shampoo or Shower Gel

A cosmetic composition is prepared in the form of a shampoo or shower gel which comprises a combination of the 5 following groups of components A, B, C, D and E in percentages by weight:

| Group A | |
|---|---|
| Gum xanthan | 0.8 |
| Water | QS for 100 |
| Group B | |
| Phenoxyethanol in a mixture with parabens which comprises methyl, ethyl, propyl and butyl parabens | 0.5 |
| Butylene glycol in a mixture with parabens which comprises a mixture of methyl, ethyl and propyl parabens | 0.5 |
| Group C | |
| Citric acid | 0.8 |
| Group D | |
| Sodium laureth sulfate | 40.0 |
| Group E | |
| Composition of Example 5 of the invention | 0.01–10% |

Carried out first of all by dissolving the gum xanthan in the water at ambient temperature and then progressively heating until a temperature of about 75° C. is reached, cooling is allowed to ambient temperature.

The pre-mixed components of group B, then of group C, then of group D and finally of group E are then added.

This composition can be used which is in the form of a shampoo or shower gel on all areas of the body that are desired to treat for a melanogenesis-inhibiting effect or depigmentation effect.

EXAMPLE 12 OF THE INVENTION

Cosmetic or Pharmaceutical Composition According to the Invention in the Form of an Aqueous Gel of the Eye Contour Type, a Body Gel This composition is prepared by mixing the following active ingredients, in percentage by weight:

| | |
|---|---|
| Composition of the invention of Example 5 | 0.01–10 |
| Carbomer | 0.5 |
| Butylene glycol | 15 |
| Phenoxyethanol in a mixture with parabene including mixtures of methyl, ethyl, propyl and butyl parabens | 0.5 |
| Water | QS for 100 |

This composition is prepared in a conventional manner by firstly mixing the composition of Example 5 with the butylene glycol, the phenoxyethanol in a mixture with the parabenses, and the water and then finally by adding the carbomer in thus obtaining an aqueous gel which can be applied onto the areas of the body for which a tyrosinase-inhibiting effect, hence melanogenesis-inhibiting effect or depigmentation effect is sought after, such as eye contours.

In this composition, the carbomer is dispersed in the water at ambient temperature and then heat is given progressively to about 75° C. under vigorous stirring and this temperature is maintained under stirring for about 30 minutes until the formation of the gel.

Cooling is then allowed to about 30° C. and then the butylene glycol is added, then the phenoxyethanol in the parabenses, and finally the composition according to the invention. It is to be noted that for each one of the preceding compositions of Examples 9 to 12, the composition of Example 5 can be replaced by any other product according to the invention.

EXAMPLE 13 OF THE INVENTION

Demonstration Test of the Anti-Tyrosinase Activity of the Products of the Invention Incorporated in Cosmetic or Pharmaceutical Compositions The sodium sulfite at a concentration of 5% such as indicated in Example 1, Table II, either alone or in a mixture with 10% mulberry extract or with 20% lemon extract, or even sodium metabisulfite at the concentration of 5% in demineralized water were incorporated separately at about 30% into the water-in-oil emulsion of Example 9, so as to obtain a concentration of 1% in this formulation.

After cooling to ambient temperature, the anti-tyrosinase activity of the formulations is evaluated.

In order to do this, 100 g of a 20% NaCl aqueous solution are added to 100 g of each one of the cosmetic or pharmaceutical formulations which were obtained with the products of the invention. The whole obtained was homogenized for 10 minutes under very strong stirring and then centrifuged at 6,000 rpm for 60 minutes.

The aqueous phase is recovered and the anti-tyrosinase activity is detected by the method described in Example 1.

The anti-tyrosinase activity, such as evaluated on the products of the invention of Example 1 incorporated in cosmetic or pharmaceutical compositions, was detected for each one of them to be 95–100%.

The same anti-tyrosinase activity evaluation is carried out 30 days, 60 days and 90 days after the manufacture.

No decrease in the anti-tyrosinase activity could be detected, this showing the very high stability of the tyrosinase.

Naturally, the invention comprises all technical equivalents of the means described, as well as their various combinations.

What is claimed is:

1. A method for inhibiting melanogenesis or for depigmenting, comprising topically delivering a melanogenesis-inhibiting or depigmenting effective amount of a melanogenesis-inhibiting or depigmenting agent consisting essentially of at least one sulfite in an amount of at least 0.01% by weight, onto areas of an animal in need thereof.

2. The method of claim 1, wherein said animal is a human being.

3. The method of claim 1, wherein said sulfite is a metabisulfite.

4. The method of claim 1, wherein said sulfite is selected from the group consisting of an alkali metal sulfite and an alkaline earth metal sulfite.

5. The method of claim 4, wherein said alkali metal sulfite is selected from the group consisting of sodium sulfite and potassium sulfite.

6. The method of claim 1, wherein the sulfite is present in the agent in an amount of between 0.01% and 20% by weight.

7. The method of claim 1, wherein the sulfite is present in the agent in an amount of between 0.01% and 10% by weight.

8. A method for inhibiting melanogenesis or for depigmenting, comprising topically delivering a melanogenesis-inhibiting or depigmenting effective amount of a melanogenesis-inhibiting or depigmenting agent consisting essentially of at least one sulfite in an amount of at least 0.01% by weight and a plant extract, said plant extract being present in an amount effective to substantially eliminate odor of the sulfite, onto areas of an animal in need thereof.

9. The method of claim 8, wherein said animal is a human being.

10. The method of claim 9, wherein the sulfite is present in an amount between 0.01% and 10% by weight.

11. The method of claim 8, wherein said sulfite is selected from the group consisting of alkali metal sulfites and alkaline earth metal sulfites, in an amount between 0.01% and 20% by weight.

12. The method of claim 8, wherein said plant extract is selected from the group consisting of a mulberry extract, a lemon extract, a saxifrage extract, a grapefruit extract, a grape extract, an oughon extract, and mixtures thereof.

13. The method of claim 8, wherein said plant extract is present in an amount of about 5% to 70% by weight.

14. The method of claim 8, wherein said plant extract is present in a composition in an amount of about 5% to about 30% by weight.

15. A method for inhibiting melanogenesis or for depigmenting, comprising topically delivering a melanogenesis-inhibiting or depigmenting agent consisting essentially of from 0.01 weight % to about 5 weight % of at least one sulfite, onto areas of an animal in need thereof.

16. The method of claim 15, wherein said animal is a human being.

17. A method for cosmetic care for inhibiting melanogenesis or for depigmenting, comprising topically delivering a melanogenesis-inhibiting or depigmenting agent consisting essentially of from 0.01 weight % to about 20 weight % of at least one sulfite, in a topically cosmetically acceptable excipient, onto an area of a human in need thereof.

18. The method of claim 17, wherein said sulfite is selected from the group consisting of alkali metal sulfites and alkaline earth metal sulfites, in an amount between 0.01 and 10% by weight.

19. The method of claim 17, wherein the amount of sulfite is between 0.01% and 5% by weight.

20. The method of claim 17, wherein the excipient further comprises a plant extract selected from the group consisting of a mulberry extract, a lemon extract, a saxifrage extract, a grapefruit extract, a grape extract, an oughon extract, and mixtures thereof, in an amount effective to substantially eliminate odor of sulfite.

21. The method of claim 20, wherein said plant extract is present in a composition in an amount of about 5% to 70% of the total weight of the agent and excipient.

22. The method of claim 21, wherein said plant extract is present in the composition at an amount of about 5% to about 30% of the total weight of the agent and excipient.

23. A method for therapeutical treatment for inhibiting melanogenesis or for depigmenting, comprising topically delivering a melanogenesis-inhibiting or depigmenting agent consisting essentially of from 0.01 weight % to about 20 weight % of at least one sulfite and a topically therapeutically acceptable excipient, onto areas of an animal in need thereof.

24. The method of claim 23, wherein said sulfite is selected from the group consisting of alkali metal sulfites and alkaline earth metal sulfites, in an amount of between 0.01% and 10% by weight.

25. The method of claim 23, wherein the amount of sulfite is between 0.01% and 5% by weight.

26. The method of claim 23, wherein the excipient further comprises a plant extract selected from the group consisting of a mulberry extract, a lemon extract, a saxifrage extract, a grapefruit extract, a grape extract, an oughon extract, and mixtures thereof, in an amount effective to substantially eliminate odor of sulfite.

27. The method of claim 26, wherein said plant extract is present in an amount of about 5% to 70% of the total weight of the agent and excipient.

28. The method of claim 26, wherein said plant extract is present in an amount of about 5% to about 30% of the total weight of the agent and excipient.

29. A method for cosmetic care for inhibiting melanogenesis or for depigmenting, comprising topically delivering onto an area of a human in need thereof a composition consisting essentially of about 5% by weight of a sulfite selected from the group consisting of sodium sulfite, potassium sulfite and sodium metabisulfite, from 10% to 20% by weight of a plant extract selected from the group consisting of mulberry extract, lemon extract, saxifrage extract, grapefruit extract, and oughon extract, and a cosmetically acceptable excipient, said composition having substantially no odor of sulfite.

30. The method of claim 29, wherein said composition consists essentially of about 5% by weight of sodium sulfite, about 10% by weight of mulberry extract and a cosmetically acceptable excipient.

31. The method of claim 29, wherein said composition consists essentially of about 5% by weight of sodium sulfite, about 20% by weight of lemon extract and a cosmetically acceptable excipient, said composition having substantially no odor of sulfite.

32. The method of claim 29, wherein said composition consists essentially of about 5% of sodium metabisulfite, about 20% by weight of saxifrage extract and a cosmetically acceptable excipient, said composition having substantially no odor of sulfite.

33. The method of claim 29, wherein said composition consists essentially of about 5% by weight of sodium metabisulfite, about 10% by weight of grapefruit extract and a cosmetically or pharmaceutically acceptable excipient, said composition having substantially no odor of sulfite.

34. The method of claim 29, wherein said composition consists essentially of about 5% by weight of potassium sulfite, about 20% by weight of grape extract and a cosmetically acceptable excipient, said composition having substantially no odor of sulfite.

35. The method of claim 29, wherein said composition consists essentially of about 5% by weight of potassium sulfite, about 10% by weight of oughon extract and a cosmetically acceptable excipient, said composition having substantially no odor of sulfite.

36. The method of claim 29, wherein said composition consists essentially of about 5% by weight of potassium metabisulfite, about 10% by weight of saxifrage extract and a cosmetically acceptable excipient, said composition having substantially no odor of sulfite.

37. The method of claim 29, wherein said composition consists essentially of about 5% by weight of potassium metabisulfite, about 5% by weight of oughon extract, about 10% by weight of grapefruit extract and a cosmetically acceptable excipient, said composition having substantially no odor of sulfite.

38. A composition comprising a cosmetically or pharmaceutically acceptable excipient, and a melanogenesis inhibiting or depigmenting agent consisting of about 5% by weight of a sulfite selected from the group consisting of sodium sulfite, potassium sulfite and sodium metabisulfite, and from 10% to 20% by weight of a plant extract selected from the group consisting of mulberry extract, lemon extract, saxifrage extract, grapefruit extract, and oughon extract, said composition having substantially no odor of sulfite.

39. A composition comprising a cosmetically or pharmaceutically acceptable excipient, and a melanogenesis inhibiting or depigmenting agent consisting of about 5% by weight of sodium sulfite and about 10% by weight of mulberry extract, said composition having substantially no odor of sulfite.

40. A composition comprising a cosmetically or pharmaceutically acceptable excipient, and a melanogenesis inhibiting or depigmenting agent consisting of about 5% by weight of sodium sulfite and about 20% by weight of lemon extract, said composition having substantially no odor of sulfite.

41. A composition comprising a cosmetically or pharmaceutically acceptable excipient, and a melanogenesis inhibiting or depigmenting agent consisting of about 5% of sodium metabisulfite and about 20% by weight of saxifrage extract, said composition having substantially no odor of sulfite.

42. A composition comprising a cosmetically or pharmaceutically acceptable excipient, and a melanogenesis inhibiting or depigmenting agent consisting of about 5% by weight of sodium metabisulfite and about 10% by weight of grapefruit extract, said composition having substantially no odor of sulfite.

43. A composition comprising a cosmetically or pharmaceutically acceptable excipient, and a melanogenesis inhibiting or depigmenting agent consisting of about 5% of potassium sulfite and about 20% by weight of grape extract, said composition having substantially no odor of sulfite.

44. A composition comprising a cosmetically or pharmaceutically acceptable excipient, and a melanogenesis inhibiting or depigmenting agent consisting of about 5% by weight of potassium sulfite and about 10% by weight of oughon extract, said composition having substantially no odor of sulfite.

45. A composition comprising a cosmetically or pharmaceutically acceptable excipient, and a melanogenesis inhibiting or depigmenting agent consisting of about 5% by weight of potassium metabisulfite and about 10% by weight of saxifrage extract, said composition having substantially no odor of sulfite.

46. A composition comprising a cosmetically or pharmaceutically acceptable excipient, and a melanogenesis inhibiting or depigmenting agent consisting of about 5% by weight of potassium metabisulfite, about 5% by weight of oughon extract and about 10% by weight of grapefruit extract, said composition having substantially no odor of sulfite.

* * * * *

UNITED STATES PATENT AND TRADEMARK OFFICE
CERTIFICATE OF CORRECTION

PATENT NO. : 5,989,596
DATED : November 23, 1999
INVENTOR(S) : DELPHINE BRESSON-RIVAL et al It is certified that error appears in the above-indentified patent and that said Letters Patent is hereby corrected as shown below:

On the title page, under "U.S. PATENT DOCUMENTS" insert:

--5,773,014  6/1998  Perrier et al......424/401--.

Signed and Sealed this

Sixth Day of March, 2001

Attest:

NICHOLAS P. GODICI

Attesting Officer

Acting Director of the United States Patent and Trademark Office